(12) United States Patent
Sjöblom et al.

(10) Patent No.: US 7,689,539 B2
(45) Date of Patent: Mar. 30, 2010

(54) SYSTEMS FOR FAST EFFICIENT RETRIEVAL OF MEDICAL IMAGE DATA FROM MULTIDIMENSIONAL DATA SETS, RELATED METHODS AND COMPUTER PRODUCTS

(75) Inventors: Erik Sjöblom, Linköping (SE); Claes Lundström, Linköping (SE)

(73) Assignee: Sectra AB, Linkoping (SE)

( * ) Notice: Subject to any disclaimer, the term of this patent is extended or adjusted under 35 U.S.C. 154(b) by 404 days.

(21) Appl. No.: 11/560,889

(22) Filed: Nov. 17, 2006

(65) Prior Publication Data

US 2007/0130165 A1    Jun. 7, 2007

Related U.S. Application Data

(60) Provisional application No. 60/738,891, filed on Nov. 22, 2005.

(51) Int. Cl.
*G06F 7/00* (2006.01)
(52) U.S. Cl. .......................................... 707/2
(58) Field of Classification Search .................. 707/2
See application file for complete search history.

(56) References Cited

U.S. PATENT DOCUMENTS

| | | | |
|---|---|---|---|
| 2002/0198454 A1* | 12/2002 | Seward et al. | 600/437 |
| 2003/0033125 A1* | 2/2003 | Picone et al. | 703/2 |
| 2004/0122702 A1* | 6/2004 | Sabol et al. | 705/2 |
| 2004/0133927 A1* | 7/2004 | Sternberg et al. | 725/136 |

OTHER PUBLICATIONS

Cignoni et al. "Multiresolution Representation and Visualization of Volume Data" *IEEE Transactions on Visualization and Computer Graphics* 3(4):352-369 (1997).
Hashimoto et al. "Hierarchical Structure for Data Transmission of Volumetric Medical Images Using Three-dimensional Wavelet Transform" *Nuclear Science Symposium Conference Record* 3:1399-1403 (2001).

(Continued)

*Primary Examiner*—Charles Rones
*Assistant Examiner*—Fazlul Quader
(74) *Attorney, Agent, or Firm*—Myers Bigel Sibley & Sajovec, P.A.

(57) ABSTRACT

Data retrieval systems for retrieving data from a multidimensional medical data set include: (a) a client configured to electronically request image data of a patient; (b) a server in communication with a plurality of electronically stored multidimensional patient medical image data sets; and (c) a data retrieval interface in communication with the client and the server. The data retrieval interface is configured to retrieve image data from the multidimensional data sets. The respective data sets have a number of grid points in G dimensions and a number of values V for each grid point. Some of the data sets have different G dimensions and V values than others. The data retrieval interface is configured to employ an object oriented retrieval process. The client can employ and Image region object to request data and the interface can employ a Physical region object that defines a multi-dimensional region extent associated with a client request for data on a region of interest to retrieve relevant image data from a respective patient data set. Related signal processor circuits, computer programs and data structures for data retrievals are also described.

31 Claims, 9 Drawing Sheets

OTHER PUBLICATIONS

Kim et al. "An efficient image data format for lossless compression and its application to interactive viewing" *International Conference on Image Processing* 1:73-76 (1996).

Linsen et al. "Hierarchical Respresentation of Time-varying Volume Data with 4 $\sqrt{2}$ Subdivision and Quadrilinear B-Spline Wavelets" *Proceedings of the 10$^{th}$ Pacific Conference on Computer Graphics and Applications*, 10 pages (2002).

Ljung et al. "Transfer Function Based Adaptive Decompression for Volume Rendering of Large Medical Data" *IEEE Symposium on Volume Visualization and Graphics* 4:25-32 (2004).

\* cited by examiner

SYSTEMS FOR FAST EFFICIENT RETRIEVAL OF MEDICAL IMAGE DATA FROM MULTIDIMENSIONAL DATA SETS, RELATED METHODS AND COMPUTER PRODUCTS

RELATED APPLICATIONS

This application claims the benefit of priority of U.S. Provisional Patent Ser. No. 60/738,891, filed Nov. 22, 2005, the contents of which are hereby incorporated by reference as if recited in full herein.

FIELD OF THE INVENTION

The present invention relates to medical renderings of imaging data.

BACKGROUND OF THE INVENTION

Two-dimensional (2-D) and three-dimensional (3-D) visualization products for providing medical images can employ rendering techniques to create images from stored electronic data files. The data input used to create the image renderings can be a stack of image slices from a desired imaging modality, for example, a Computed Tomography (CT) or Magnetic Resonance (MR) modality. The visualization can convert the image data into an image volume to create renderings that can be displayed on a workstation display.

Slice-by-slice viewing of medical data may be increasingly difficult for the large data sets now provided by imaging modalities, raising issues of information and data overload and clinical feasibility with current radiology staffing levels. See, e.g., *Addressing the Coming Radiology Crisis: The Society for Computer Applications in Radiology Transforming the Radiological Interpretation Process (TRIP™) Initiative*, Andriole et al., at URL scarnet.net/trip/pdf/TRIP_White_Paper.pdf (November 2003). In some modalities, patient data sets can have large volumes, such as greater than 1 gigabyte, and can even commonly exceed 10's or 100's of gigabytes, hence terabytes of data in a patient multi-dimensional data set is becoming more common.

The diagnostic task of a clinician such as a radiologist can vary patient to patient and, accordingly so can the desired renderings or views of the medical images of the patient. In some visualization systems, a physician uses an interactive workstation that has a data retrieval interface that obtains the medical data for medical image renderings from electronic volume data sets to generate desired medical representations. Image visualizations using the multi-dimensional image data can be carried out using any suitable system such as, for example, PACS (Picture Archiving and Communication System). PACS is a system that receives images from the imaging modalities, stores the data in archives, and distributes the data to radiologists and clinicians for viewing.

Unfortunately, the size of medical volume data sets can inhibit rapid visualization times, particularly with a resolution sufficient for diagnostic purposes. In some cases, interactive image generation of multi-resolution representations may not be feasible using conventional processing techniques even with the use of fast graphic hardware. Two common methods for creating multi-resolution representations are well known to those of skill in the art as a straightforward sub-sampling and a wavelet-based decomposition. See Kim et al., *An Efficient Data Format For Lossless Compression and It's application to Interactive Viewing*, 0-7803-3258-X/96, IEEE (1996) and Hashimoto et al., *Hierarchical Structure for Data Transmission of Volumetric Medical Images Using Three-Dimensional Wavelet Transform*, 0-7803-7324-3/02, IEEE, pp. 1399-1403 (2002). It is also known to employ a lower resolution to reduce data, for example, a "level-of-detail" (LoD) is a very well known term within visualization. For a general description of different data handling techniques including LoD, ad hoc data organizations, approximation techniques, subsampling, and multiresolution representation, see Cignoni et al., *Multi-resolution Representation and Visualization of Volume Data*, 1077-2626/97, IEEE (1997) (proposing the use of tetrahedral meshes to represent and visualize scalar volume data at multiple resolution).

Despite the above, there remains a need for alternate efficient data retrieval interface systems for rendering image volumes using multi-dimensional data sets.

SUMMARY OF EMBODIMENTS OF THE INVENTION

Embodiments of the present invention are directed to methods, systems and computer program products that can allow rapid retrieval of data from multi-dimensional data sets, the data having arbitrary extent and resolution in all dimensions. Embodiments of the present invention are able to handle arbitrarily sized data sets, regardless of client hardware and network bandwidth (assuming that the data set fits into disk space at a server.) The data retrieval and/or transmittal can be carried out so that a full amount of data is not generally sent to a client using a data interface to handle the data sorting upstream of the client.

Embodiments of the invention are directed to a retrieval interface for multi-dimensional data as such, rather than specific data representations or image visualizations. Indeed, the end visualization may appear the same as conventional visualizations, but can be rendered with increased speed and/or using novel data retrieval methodology.

Being able to select retrieval of arbitrary extent and resolution in multiple dimensions can allow the output image data to be adapted to a current need, avoiding the performance penalty of sending data that will not be used anyway. This penalty can be prohibitive for a whole visualization application, e.g., for medical imaging where the standard data set sizes are rapidly increasing.

Embodiments of the invention are particularly suitable for PACS, however, the invention is, however, more generally applicable, and should not be interpreted to be limited to PACS.

Some embodiments are directed to data retrieval systems for retrieving data from a multidimensional medical data set. The systems include: (a) a client configured to electronically request image data of a patient; (b) a server in communication with a plurality of electronically stored multidimensional patient medical image data sets; and (c) a data retrieval interface in communication with the client and the server. The data retrieval interface is configured to retrieve image data from the multidimensional data sets. The respective data sets have a number of grid points in G dimensions and a number of values V for each grid point. Some of the data sets have different G dimensions and V values than others. The data retrieval interface is configured to employ a Physical region object that defines a multi-dimensional region extent associated with a client request for data on a region of interest to retrieve relevant image data from a respective patient data set.

Other embodiments are directed to signal processor circuits in communication with a client and a server for extracting data from respective patient multidimensional imaging data sets obtained from different imaging modalities. The signal processor circuit is configured to define a Physical region object to retrieve a subset of data from a respective multi-dimensional patient image data set that is accessible via the server.

Still other embodiments are directed to signal processor circuits in communication with a client. The signal processor circuit is configured to define an Image data region object that is electronically transmitted to a server in communication with electronically stored multidimensional patient data sets to request image data from a target patient multidimensional imaging data set.

Other embodiments are directed to signal processor circuits that include a data retrieval interface module for extracting data from respective patient multidimensional imaging data sets obtained from different imaging modalities. The data retrieval interface module is configured to electronically determine on-the-fly a sampling grid used to retrieve image data from the multidimensional imaging data. The data regarding the sampling grid used to retrieve the image data is transmitted to a client along with the retrieved image data.

In some embodiments, the data retrieval module can be configured to access different data sets with some of the data sets have grid points in G dimensions such that $G \leq 4$ and at least some have multivariate values for each grid point such that $1 < V \leq 6$ while others have a single value for a respective grid point, $V=1$ and/or the data retrieval module may be configured to determine the number V of a patient multi-dimensional data set on-the-fly and does not assume a static ordering of slices or a static number for V.

Still other embodiments are directed to medical image systems that include an object-oriented data retrieval module. The data retrieval module is configured to: (a) receive a single image data region query from a physician workstation to initiate a data retrieval operation, the single query defining resolution, quality and multi-dimensional coordinates a region of interest; and (b) electronically retrieve relevant patient image data from a multi-dimensional data set, then transmit the relevant data to the workstation with data regarding a sampling grid employed to obtain the relevant patient image data.

In some embodiments, the data retrieval module may be configured to determine a sampling grid used to retrieve image data based on an on-the-fly algorithm corresponding to a type of data set, an end representation view, and a size of a viewport on a display at a workstation.

Other embodiments are directed to computer program products for providing physician interactive access to patient medical volume data for retrieving data for rendering diagnostic medical images. The computer program product includes a computer readable storage medium having computer readable program code embodied in the medium. The computer-readable program code includes: (a) computer readable program code configured to generate a first object to request image data, the first object being associated with a viewing specification of an image data region of interest from at least one client; (b) computer readable program code configured to generate a second object associated with an electronic physical specification based on data from the viewing specification; and (c) computer readable program code configured to retrieve relevant patient image data from a server having digital multi-dimensional patient image data sets using data from at least one of the first and second objects.

The computer readable program can be configured to retrieve relevant data is configured to alter, on-the-fly, a sampling grid and/or resolution requested by a respective client.

Still other embodiments are directed to data structures in a medical visualization system that represents an object used by clients of a networked system to request image data of a region of interest. The data structures include a first object that represents a request for multi-dimensional image data of a patient for an image data region of interest, the first object identifying coordinates of a multi-dimensional region of interest, a proposed sampling grid and/or resolution and suggested quality for each dimension associated with the requested image data.

Other embodiments are directed to data structures in a medical visualization system that represents an object used by a data retrieval interface or server of a networked system to retrieve image data of a patient multidimensional data set. The structures include: (a) a first object that represents a spatial extent of a physical region of a region of interest identified in a call from a client; and (b) a second object that represents an overlay that can electronically associate text and/or graphic data with views of data in the physical region of interest.

In particular embodiments, the data structures can also include a third object that represents a frame of reference associated with the physical region in the patient data set; and a fourth object that represents a variate sorting rule that defines how multivariate data is to be grouped or sorted.

It is noted that any of the features claimed with respect to one type of claim, such as a system, apparatus, or computer program, may be claimed or carried out as any of the other types of claimed operations or features.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EMBODIMENTS OF THE INVENTION

Figure 1:
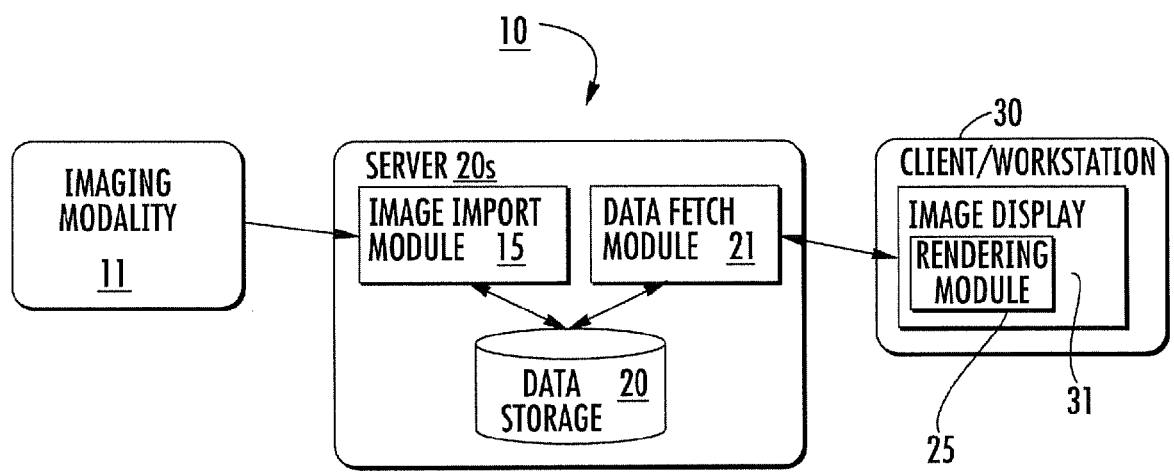
FIG. 1 is a schematic diagram of an electronic visualization system that can be used to render and display medical images

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. In the claims, the claimed methods are not limited to the order of any steps recited unless so stated thereat.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "Direct Volume Rendering" or DVR is well known to those of skill in the art. DVR comprises electronically rendering a medical image directly from data sets to thereby display visualizations of target regions of the body, which can include color as well as internal structures, using multi-dimensional 3D or 4D or more dimensional data. In contrast to conventional iso-surface graphic constructs, DVR does not require the use of intermediate graphic constructs (such as polygons or triangles) to represent objects, surfaces and/or boundaries. However, DVR can use mathematical models to classify certain structures and can use graphic constructs.

Also, although embodiments of the present invention are directed to DVR of medical images, other 3-D image generation techniques and other 3-D image data may also be used. That is, the 3-D images with respective visual characteristics or features may be generated differently when using non-DVR techniques.

The term "automatically" means that the operation can be substantially, and typically entirely, carried out without human or manual input, and is typically programmatically directed or carried out. The term "electronically" includes both wireless and wired connections between components.

The term "clinician" means physician, radiologist, physicist, or other medical personnel desiring to review medical data of a patient. The term "tissue" means blood, cells, bone and the like. "Distinct or different tissue" or "distinct or different material" means tissue or material with dissimilar density or other structural or physically characteristic. For example, in medical images, different or distinct tissue or material can refer to tissue having biophysical characteristics different from other (local) tissue. Thus, a blood vessel and spongy bone may have overlapping intensity but are distinct tissue. In another example, a contrast agent can make tissue have a different density or appearance from blood or other tissue.

Visualization means to present medical images to a user/clinician for viewing. The visualization can be in a flat 2-D and/or in 2-D what appears to be 3-D images on a display, data representing features with different visual characteristics such as with differing intensity, opacity, color, texture and the like. The images as presented by the visualization do not have to be the same as the original construct (i.e., they do not have to be the same 2-D slices from the imaging modality). Two common visualization techniques (apart from viewing original slices) are Multiplanar Reconstruction (MPR), which shows an arbitrary oblique slice through the anatomy and Maximum Intensity Projection (MIP) where a slab is visualized by displaying the maximum value "seen" from each image pixel. For MPR, there are a number of variants, the slice can be thin or constructed by averaging a thicker slab, etc . . . .

The term "similar examination type" refers to corresponding anatomical regions or features in images having diagnostic or clinical interest in different data sets corresponding to different patients (or the same patient at a different time). For example, but not limited to, a coronary artery, organs, such as the liver, heart, kidneys, lungs, brain, and the like.

A data set can be defined as a number of grid points in G dimensions, where there is V number of values in each grid point. The term "multi-dimensional" refers to both components, grid G and variates V, of the data sets. For data sets having a $V \geq 1$, the data set is referred to as multi-variate. Examples: a normal medical data set has G=3 and V=1, a normal time-dependent volume has G=4 and V=1, a volume describing flow will have G=3 and V=3 (three values, since the velocity is a 3D vector). The data sets of the instant invention for medical images will typically have G and V values of: $G \leq 4$ and $V \leq 6$. As known to those of skill in the art, traditional medical systems are bound by the 2D slice format used by the imaging modalities and use this base to construct higher-dimensional data.

In the description that follows, a client-server setup is illustrated, but the data retrieval interfaces contemplated by the instant invention may be implemented within one computer as well. The term "client" will be used both to denote a computer and the software (application) running on the computer. Additional computers can be used including more than one server and/or more than one client for a workstation. For example, the server can be more than one server with different functions carried out by or between different servers, such as the patient data storage can be on one or more separate servers.

Some embodiments employ object-oriented software to carry out operations of the invention. The term "object-oriented" with reference to programming or software refers to "objects" that receive and/or send messages. As is well known, the "object" contains code (sequences of computer instructions) and data (information which the instructions operate on). Thus, code and data can be merged into a single indivisible thing, i.e., an "object." The communication between objects can be carried out using messages. The object which a message is sent to can be called a receiver and the messages can define the interface to an object. Everything that an object can do can be represented by its message interface.

The term "Image data region object" refers to a user data input request technique that allows a user to select a physical region of interest in a patient image to define a reference type variable as an "object" that can point to instructions and data of any data type. Typically, a user presses or selects a button like "Show images" or selects a patient in a list and the system automatically electronically determines which image data regions to request from the server. The Image data region object can be a single query input that initiates a request for image data from multidimensional data sets in electronic storage. The Image data region object can have a plurality of associated electronic parameters that can be used to allow a data retrieval interface to define a subset of relevant corresponding image data from a whole volume data set in a multidimensional and potentially multivariate data file that corresponds to the physical region of interest.

The terms "on-the-fly" and/or "sua sponte" means that the circuit or module (such as the data retrieval interface) can determine itself whether or how to apply or execute a particular action, such as, what sampling grid to employ or what resolution to apply to a client request for image data. The on-the-fly or sua sponte decision can be based on a "best-practice" algorithm that evaluates certain parameters, such as image type, view, diagnosis type, equipment, system status (i.e., the number of clients online, or is the system operating at reduced bandwidth operation due to a large number of current clients being "online") and the like.

The term "data structure" refers to a structure that has a defined relationship between executable instructions and data and may be provided as object-oriented program code and/or sequence of instructions that may be implemented in a computer readable medium.

The term "data representation" refers to data format. Exemplary representations of image data include: a stack of uncompressed 2D slices and multiple instances of a volume at different resolutions (pyramid) achieved by wavelet techniques.

Turning now to FIG. 1, a visualization system 10 is illustrated. As known to those of skill in the art, the system 10 can include at least one server 20s with an image import module 15, patient data storage 20, a data fetch module 21, a client (and/or workstation) 30 and a rendering system 25. The visualization system 10 can be in communication with at least one imaging modality 11 that electronically obtains respective volume data sets of patients and can electronically transfer the data sets to the electronic storage 20. The imaging modality 11 can be any desirable modality such as, but not limited to, NMR, MRI, X-ray of any type, including, for example, CT (computed tomography) and fluoroscopy, ultrasound, and the like. The visualization system 10 may also operate to render images using data sets from more than one of these modalities. That is, the visualization system 10 may be configured to render images irrespective of the imaging modality data type (i.e., a common system may render images for both CT and MRI volume image data). In some embodiments, the system 10 may optionally combine image data sets generated from different imaging modalities 11 to generate a combination image for a patient.

The rendering system 25 can be in communication with a physician workstation 30 to allow user input (typically graphical user input ("GUI")) and interactive collaboration of image rendering to give the physician the image views of the desired features in generally, typically substantially, real time. The rendering system 25 can be configured to zoom, rotate, and otherwise translate to give the physician visualization of the patient data in numerous views, such as section, front, back, top, bottom, and perspective views. The rendering system 25 may be wholly or partially incorporated into the physician workstation 30, or can be a remote or local module (or a combination remote and local module) component or circuit that can communicate with a plurality of physician workstations (not shown). The visualization system can employ a computer network and may be particularly suitable for clinical data exchange/transmission over an intranet. A respective workstation 30 can include at least one display 31 (and may employ two or more adjacent displays). The workstation 30 and/or rendering system 25 form part of an image processor system that includes a digital signal processor and other circuit components that allow for collaborative interactive user input using the display at the workstation 30. Thus, in operation, the image processor system renders the visualization of the medical image using the medical image volume data, typically on at least one display at the physician workstation 30.

Figure 2:
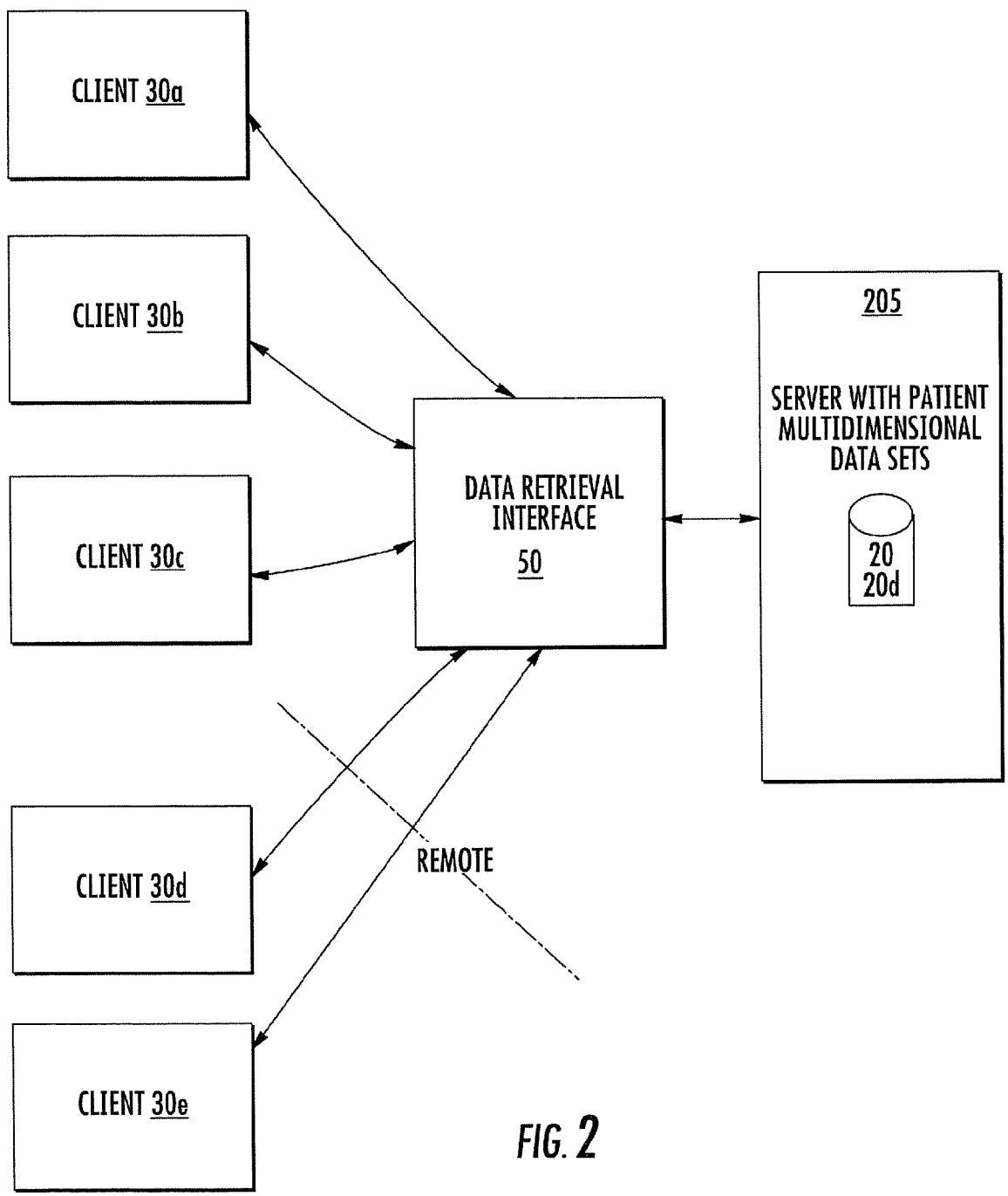
FIG. 2 is a schematic illustration of a medical imaging visualization system such as a PACS according to embodiments of the present invention.

As shown in FIG. 2, each respective workstation 30 can be described as a client 30 (shown as 30a, 30b, 30c, . . . 30e) that communicates with at least one (hub or remote) server 20s that stores the patient data sets or is in communication with the stored patient electronic data files 20. Additional numbers of clients 30 may be in communication with the server 20s and more than one server 20s may be used to store patient data. A data retrieval interface 50 can be used to communicate with the clients 30a-30e and the stored data sets on and/or accessible via server 20s. Some of the clients, shown as clients 30a, 30b, 30c can be local (within a common clinic or facility) and can access the data sets via a relatively broadband high speed connection using, for example, a LAN, while others, shown as clients 30d, 30e, designated by the broken line, may be remote and/or may have lesser bandwidth and/or speed, and for example, may access the data sets via a WAN and/or the Internet. Firewalls may be provided as appropriate for security.

For ease of discussion, the data retrieval interface 50 is shown as a stand-alone module or circuit. However, the interface 50 can be disposed partially on each client 30, partially or wholly on the server 20s, or may be configured as a discrete data retrieval interface server 50s (not shown). The clients 30, server 20s and/or interface 50 can each include a digital signal processor, circuit and/or module that can carry out aspects of the present invention. As shown in FIG. 2, all or selected ones of the clients 30a-30e can be online at the same time and may each repeatedly communicate with the data retrieval interface 50 to request volume image data, potentially resulting in a speed penalty and inhibiting fast system performance.

To inhibit this performance issue, in some embodiments, the data retrieval interface 50 can be configured to limit each client 30 to a single query that includes multiple parameters for defining desired or target image data during data retrieval of data subsets from a full volume data set. The subsets of data are associated with a physical region in an image data region of interest (as selected by the user) as will be discussed further below.

In some embodiments, the data retrieval interface 50 can communicate with and extract relevant image data from a variety of multi-dimensional data sets in the stored data 20. The multi-dimensional data sets can have different data arrangements or format types, can be from different imaging modalities, and can have multiple and different dimensions and one or more of the dimensions can be multi-variate dimensions.

Figure 4:
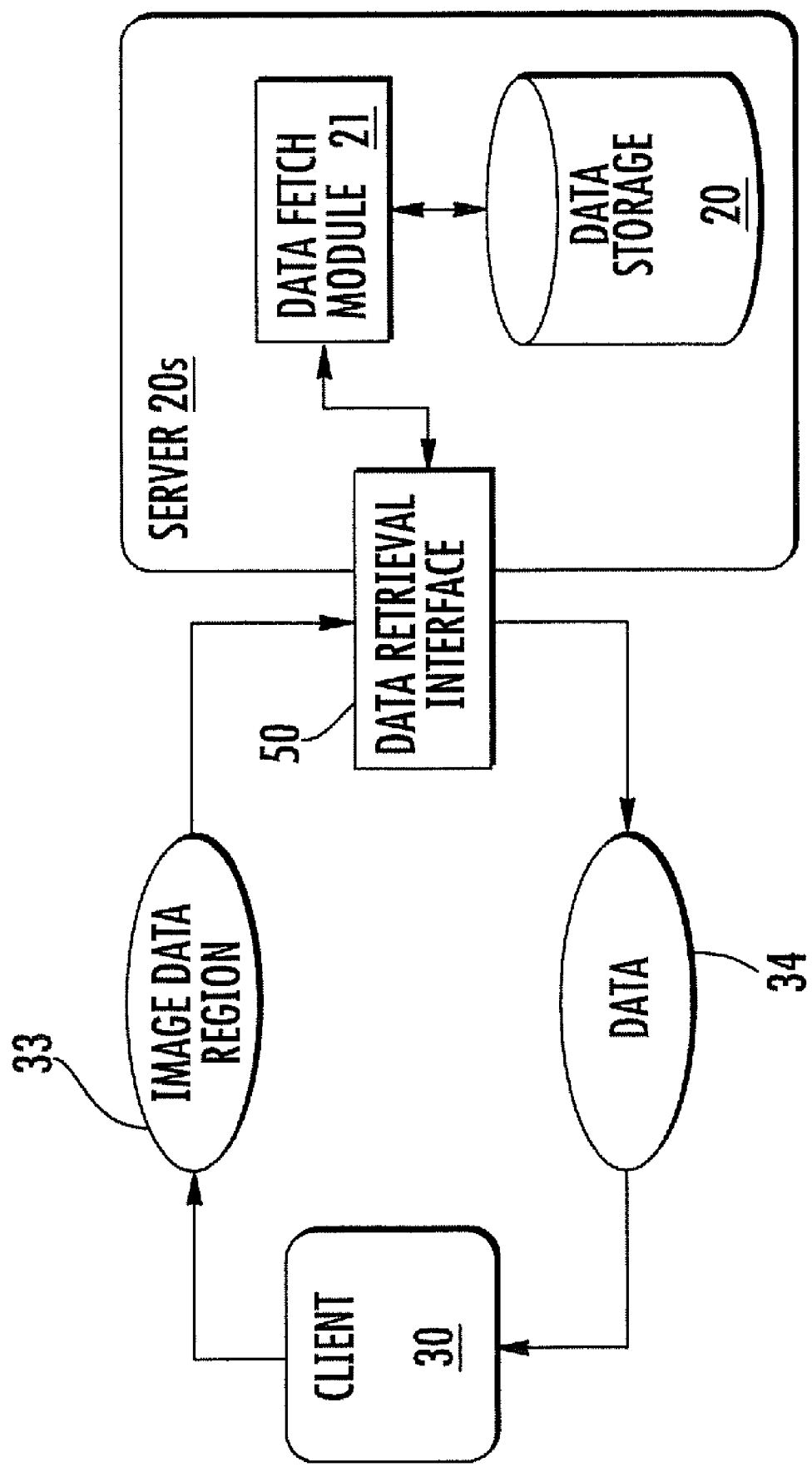
FIG. 4 is a schematic illustration of a data retrieval system according to embodiments of the present invention.

In some embodiments, as shown in FIG. 4, the data retrieval interface 50 is isolated from and/or operates independent of the representation system so that the data retrieval interface 50 can operate independently of the representation of the sampled data. That is, the data retrieval interface 50 cooperates with the respective client 30 and a data storage module 20 to select appropriate image data and forward the image data to the rendering system 25 whereby the system 25 then generates or renders the associated image and displays the image on a display 31 at a respective client or workstation 30.

Typically, an optimal data representation can depend on how the data is to be used and the technical environment (such as whether the environment can reasonably efficiently support a high resolution image). In the medical context, the optimal representation for a radiologist accessing the data over a fast network is not the same as for a clinician far from the hospital with low-bandwidth connection. Thus, a robust and long-lasting interface such as that contemplated by embodiments of the instant invention can be separated from the representation. Again, traditional systems are bound by the 2D slice format used by the imaging modalities. This separation of responsibilities and information hiding between components can employ a well-known method of object-oriented software design, hence creating flexible modular systems that can be relatively easily maintained, upgraded and/or improved over time.

In some embodiments, the data retrieval interface 50 can support an arbitrary number of both grid dimensions and values in data sets. The term "arbitrary" means not fixed and/or a number that can be defined on-the-fly. In medical imaging, data sets of $G \leqq 4$ and $V \leqq 6$ are commonly used. Traditional medical systems are bound by the 2D slice format used by the imaging modalities and therefore use this base to construct higher-dimensional data.

In some embodiments, the data interface 50 can be configured to scale well with extremely large data sets (which currently includes terabytes of data and which may grow even larger). As is known, there are two primary issues related to efficiently handling large data sets for diagnostic image renderings. The first is that it is typically desired to employ efficient ways to access subsets of the data, where the data reduction is adapted to the end-usage of the data. The second is that the meta data overhead should be minimized. For example, for a 4D data set, with a $512^3$ volume and with 1000 time frames, if represented by and accessed as 2D slices, the client 30 would generally need to know the size and position of 512,000 slices. Even though this represents a few bytes for each slice, the overhead can be very large, especially if the client 30 just wants a small region of interest in low resolution.

In some embodiments, the full data set of the patient can be accessible for data sampling, extraction, and retrieval. As is well known to those of skill in the art, there can be some relatively strict technical bottlenecks in imaging hardware, e.g., the amount of internal memory or graphics card memory. In order to be able to show the full extent of the volume, lower resolution versions are obtained. It is very inefficient to send all data to a requesting client, then calculate the low resolution version. Instead, the data retrieval interface 50 can be configured to calculate a lower resolution version of a volume prior to sending the extracted data to a client or to a rendering module, as appropriate, thus reducing the amount of data sent over the network accordingly.

In some embodiments the data retrieval interface 50 can be configured to support sort/group operations on-the-fly. Especially in MR, multi-variate data (more than one value per grid point) is common, usually in form of multiple sequences (T1, T2, PD . . . ) over the same volume. In the end review process, each physician sorts and groups these images differently, and can also apply several variants of sorting and grouping in each review. Therefore, the retrieval interface 50 can be configured so that it evaluates the V "dimension" of a multi-dimensional data set on-the-fly and does not assume a static ordering of slices or the V "dimensions".

In some embodiments, the data retrieval interface 50 can be configured to support overlays so that the overlays are not firmly connected to 2D slices and can be handled as separate objects. "Overlays" is the term in the medical imaging context for text annotations and/or graphical objects inserted into the images. Traditionally, these are connected to a specific 2D image slice. Since the 2D slice representation is no longer assumed, the overlays are handled independently of the data, as objects with specified position, extent and display characteristics.

Another reason for inducing undue system data overload or overhead is if the client 30 must send multiple data retrieval queries to the server 20s. This is particularly pertinent in PACS (such as shown in FIG. 2), where there usually is a large number of clients 30 connected to a single server 20s. To help alleviate or reduce the likelihood that the calls or queries cramp the server 20s, the client 30 can be configured to access a target data set in a single call or query. For the same reason, additional "negotiation" calls for data sets between server 20s and client 30 can be limited, if allowed at all.

Generally described, the data retrieval interface 50 can function as a 4D (four dimensional) retrieval interface, which is typical for data sets requested in medical imaging systems, where $G \geqq 4$ and $V = 1$. For some 4D data sets of interest, there are 2-3 spatial dimensions, possibly the time dimension, and one value for each grid point. These data sets are usually created as a set of 2D slices in the imaging modality, but embodiments of the instant invention are configured so as to make no assumption on which representation they are actually stored in when they are retrieved using the data retrieval interface 50.

In the proposed retrieval interface 50, the primary part of a client's 30 query to the server 20s includes three parameters or parts: (a) coordinates for a 4D region of interest; (b) suggested sampling grid (in the case of an equidistant sampling, this corresponds to the resolution) for all four dimensions; and (c) suggested quality for all four dimensions. The client 30 can determine the wanted sampling grid depending on how the data will be used. The determination may be automatically electronically determined, typically given by the size of the viewport on the display screen used to request the data. The data retrieval interface 50 and server 20s process the request and sends back the relevant image data along with the actual sampling grid chosen. The sampling grid used by the data retrieval interface 50 and server 20s is usually not the same as the one as the client 30 requested. In this way, the meta data at the client 30 is reduced. One parameter that is gleaned from the user/client is the spatial extent of the original 4D image, which is information of fixed size that does not increase by the number of original slices.

Figure 3:
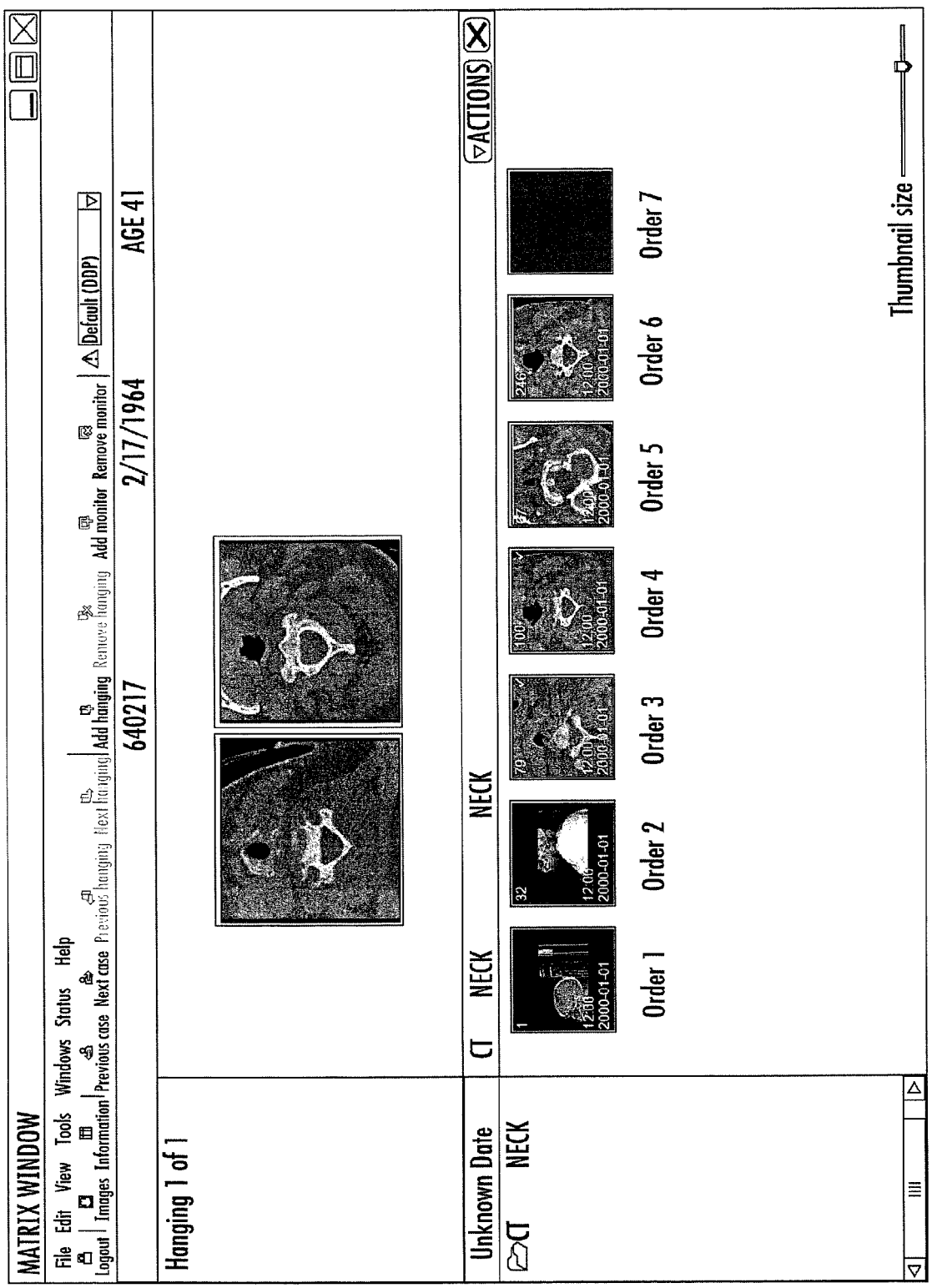
FIG. 3 is a screen shot of an examination display with view ports according to embodiments of the present invention.

FIG. 3 is a screen capture of one display of patient image data using view ports. "View port" is the term we use for the screen space an image occupies. Thumbnail images have a small viewport, etc. If the resolution of the view port is significantly smaller than the original image, the full data should not be sent, as it will be down-sampled anyway. This goes for small view ports, but there are also relatively large images like mammograms (typically about 2500×2500 pixels) that usually are down-sampled even in full screen size. FIG. 3 illustrates an examination overview window with some smaller view ports (using CT neck image data).

From a software architecture point of view, there is another benefit of this approach, namely that the data representation can be substantially completely hidden from the client 30. The whole data processing in the server 20s may change without having to change the interface 50 and/or the client 30. The interface 50 can act as insulation between the client's rendering system and the server's data fetching. In such an embodiment, the data representation (for instance multi-resolution wavelet "pyramids") is not known to the client 30, the client 30 can only access the methods exposed or allowed by the interface 50. The data fetching of the server 20s grabs the correct data and sends to the client 30.

In some embodiments, the data retrieval interface 50 described above as a 4D retrieval interface, can be extended to be a general retrieval interface that can cover an arbitrary number of dimensions G and arbitrary number of variates V. This general data retrieval interface embodiment can support queries with the following contents: (a) coordinates for a multi-dimensional region of interest; (b) suggested sampling grid or resolution in all G grid dimensions; and (c) suggested quality for all grid dimensions G and all variates V.

It is noted that the grid dimensions and variates can be handled in two primary but different ways, coupled or independent, using the data retrieval interface system described herein. In-between coupled dimensions/variates, the resolution and quality is always the same, e.g., changing the resolution for one dimension changes the resolution for all its coupled dimensions. Independent dimensions/variates, on the other hand, have independent resolution and quality. There may be several groups of coupled dimensions/variates.

As an example, consider a time-varying 2D image, three dimensions in total. Here the two spatial dimensions can be coupled to achieve an efficient representation, while the time dimension can be decoupled. If there are limited resources and there is an image where the time variation is the most interesting, the time resolution can be maximized at the expense of a low spatial resolution.

The resolution requirements do not have to be global, they can vary across the dimensions. The resolution requirements can be specified manually or determined automatically. An example of a spatially varying automatic resolution control is described in Ljung et al., *Transfer Function Based Adaptive Decompression For Volume Rendering Of Large Medical Data Sets*, Proceedings IEEE Volume Visualization And Graphics Symposium (2004), Pp. 25-32.

FIG. 4 illustrates a data retrieval process using the data retrieval interface 50. Generally described, in operation, user actions on the client 30 initiates a request, query or call to display a medical image view of a patient. The client 30 electronically determines the specification for this requested image view. The specification can be an Image data region object 33 that has electronic parameters that describe the requested region of interest, resolution, and quality. The region of interest refers to a connected physical region. The client 30 executes the data retrieval request by sending the selected Image data region object 33 to the server 20s via the data retrieval interface 50. The interface 50 may reside in the server 20s or may be a separate module in communication with the clients 30 and server 20s. The interface 50 may also reside partially in the client 30, partially in the server 20s, or other suitable locations. The server 20s fetches the requested data. The data retrieval interface 50 tries to accommodate the requested specification requirements on resolution and quality, if possible. However, the data retrieval interface 50 can override the request (not accommodate the request exactly) and it is not guaranteed that the requirements will be met, the data interface 50 can adapt the specification in order to optimize the retrieval. The extracted data 34 is sent to the client 30 (or rendering system 25 (FIG. 1)). It is also noted that the rendering system 25 can reside partially or wholly on the client 30 (or workstation) or outside the client 30 as a separate either local or remote module.

Figure 5:
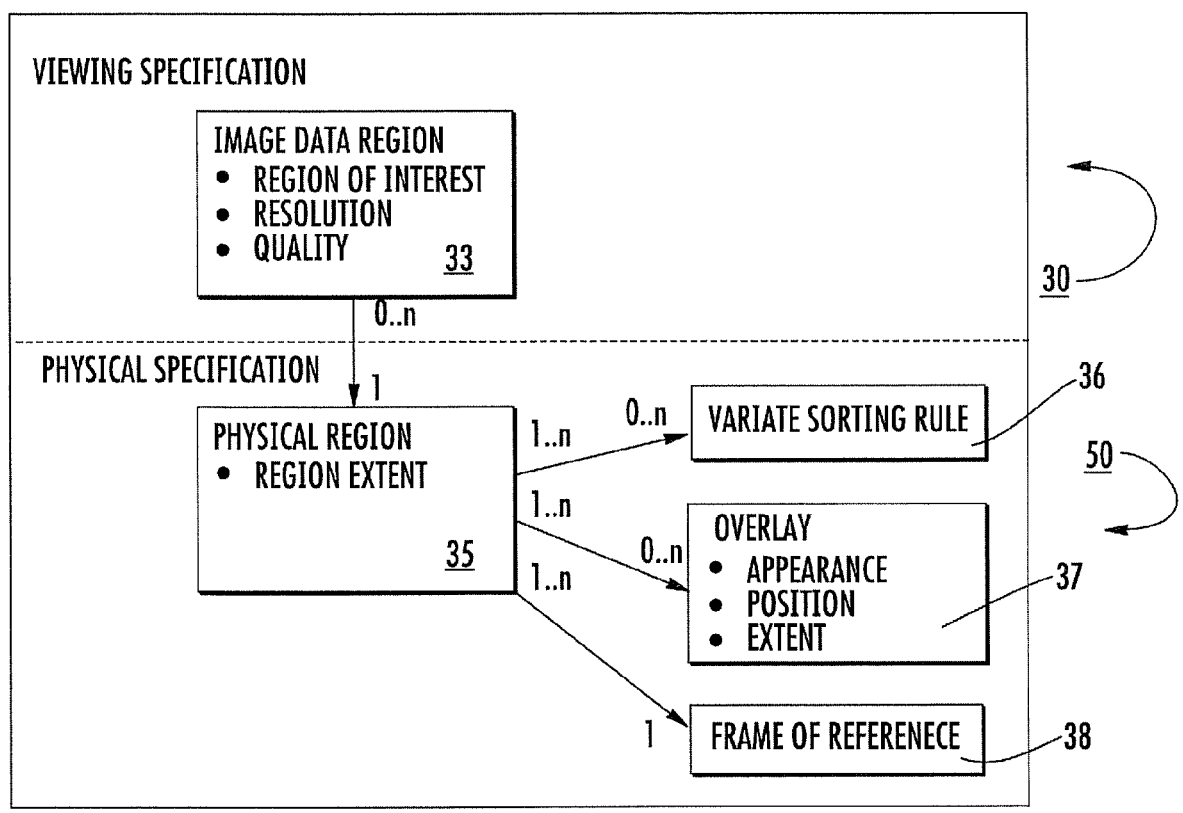
FIG. 5 is a block diagram of a viewing specification and a physical specification with exemplary data structures that can be used to retrieve data in an efficient manner according to embodiments of the present invention.

FIG. 5 schematically illustrates the objects that can be involved in data retrieval through the proposed interface 50. The Physical region object 34 represents a continuous 4D volume. The Physical region object 34 does not contain image data, it is a generalized region definition that can be used to retrieve image data. If the data set is multivariate, the sorting and grouping of the different variates can be handled by Variate sorting rule objects 36. There is the possibility to connect overlays to the region, the Overlay object 36 describes their respective appearance (bitmap, circle, line, text, etc.), and their position and extent within the region. One can generally divide 2D slice overlays into two types: bitmaps and objects. Bitmaps are "burnt" into the image and are defined in terms of image pixels. Objects are bound to a specific point in the image space, for instance an arrow pointing to some anatomy. In 2D it is relatively simple to know when to show the overlays: when the corresponding 2D slice is shown. Moving to a continuous multi (4D) representation, the data interface 50 can be configured to determine when to show them. For objects, may be shown in any region of interest containing its reference point while bitmaps may be shown only if the exact same slice is displayed. This type of decision or association can be carried out using the Overlay object with defined appearance, position, and extent. The Frame of reference object 38 connects all physical regions that have a common coordinate system. Typically there is a multitude of physical regions for each data set, which then have the same frame of reference. There is also the possibility that several data sets can have the same frame reference, for instance in fusion and registration applications.

As stated above, the Image data region object 33 contains the information which may be used to retrieve the requested data. There is a reference to a specific physical region. The Image data region object 33 can also specify a wanted region of interest within the physical region. The resolution and quality can be specified separately for each dimension (generalized dimension, both grid dimensions and the different variates).

Figure 6:
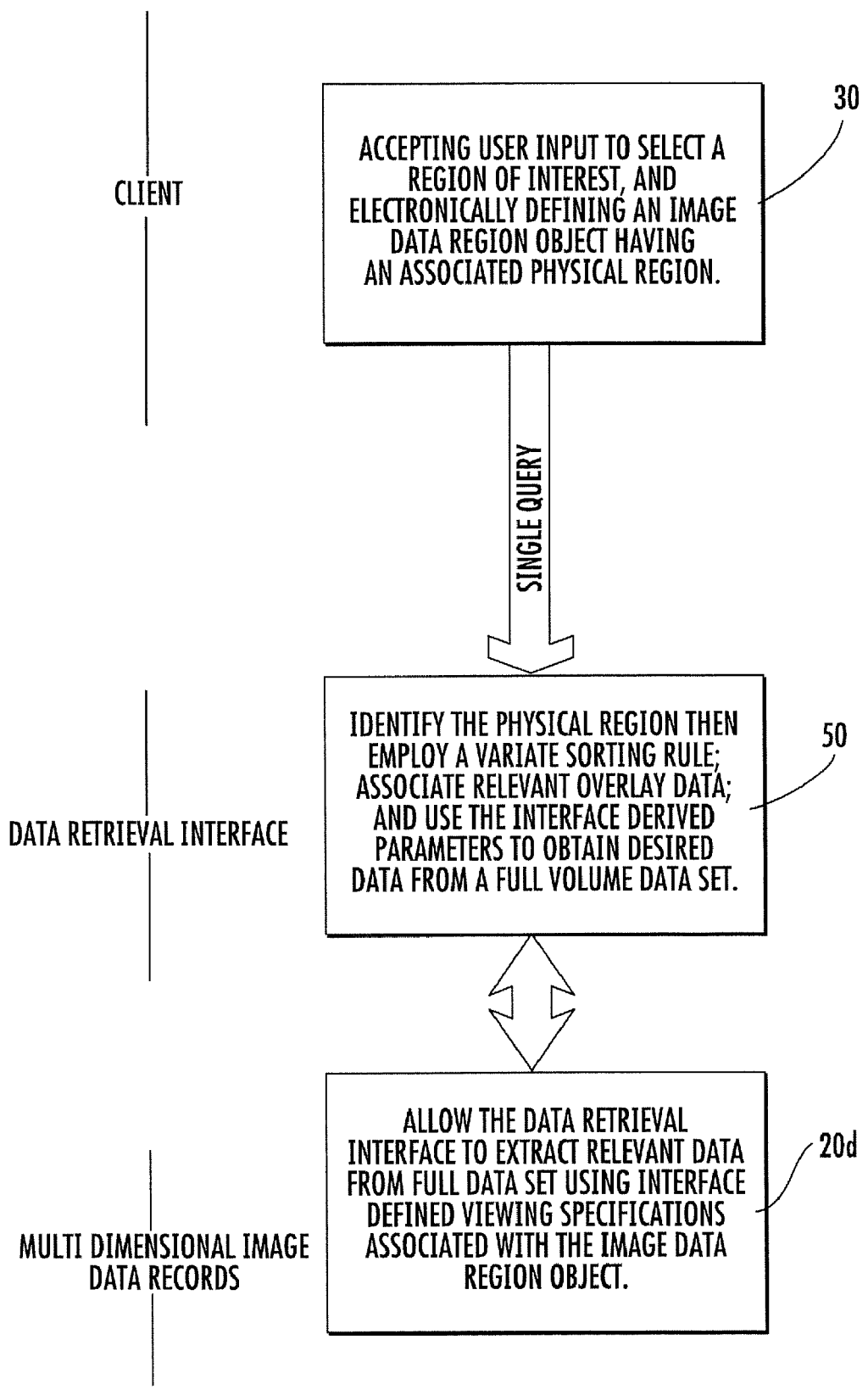
FIG. 6 is a flow chart of operations that can be performed to carry out embodiments of the present invention.

FIG. 6 illustrates operations that can be carried out at each of a client 30, a data retrieval interface 50 and at stored data records 20d to request and retrieve relevant image data. As shown, user input is accepted at a client 30 to select a region of interest and electronically define an Image data region object having an associated physical region. Then, the query or call with the Image region object is sent to the data retrieval interface 50. The interface 50 can review the object 33, identify the physical region, and apply a variate-sorting rule, as appropriate. The interface 50 can electronically associate overlay data with relevant image data (typically after extraction). Data from at least some of these actions can be used to obtain relevant data from a full volume data set in stored electronic records 20d. The data retrieval interface 50 is allowed to extract relevant data from full volume data sets using at least some of the interface defined viewing specifications associated with the Image data region object.

Figure 7:
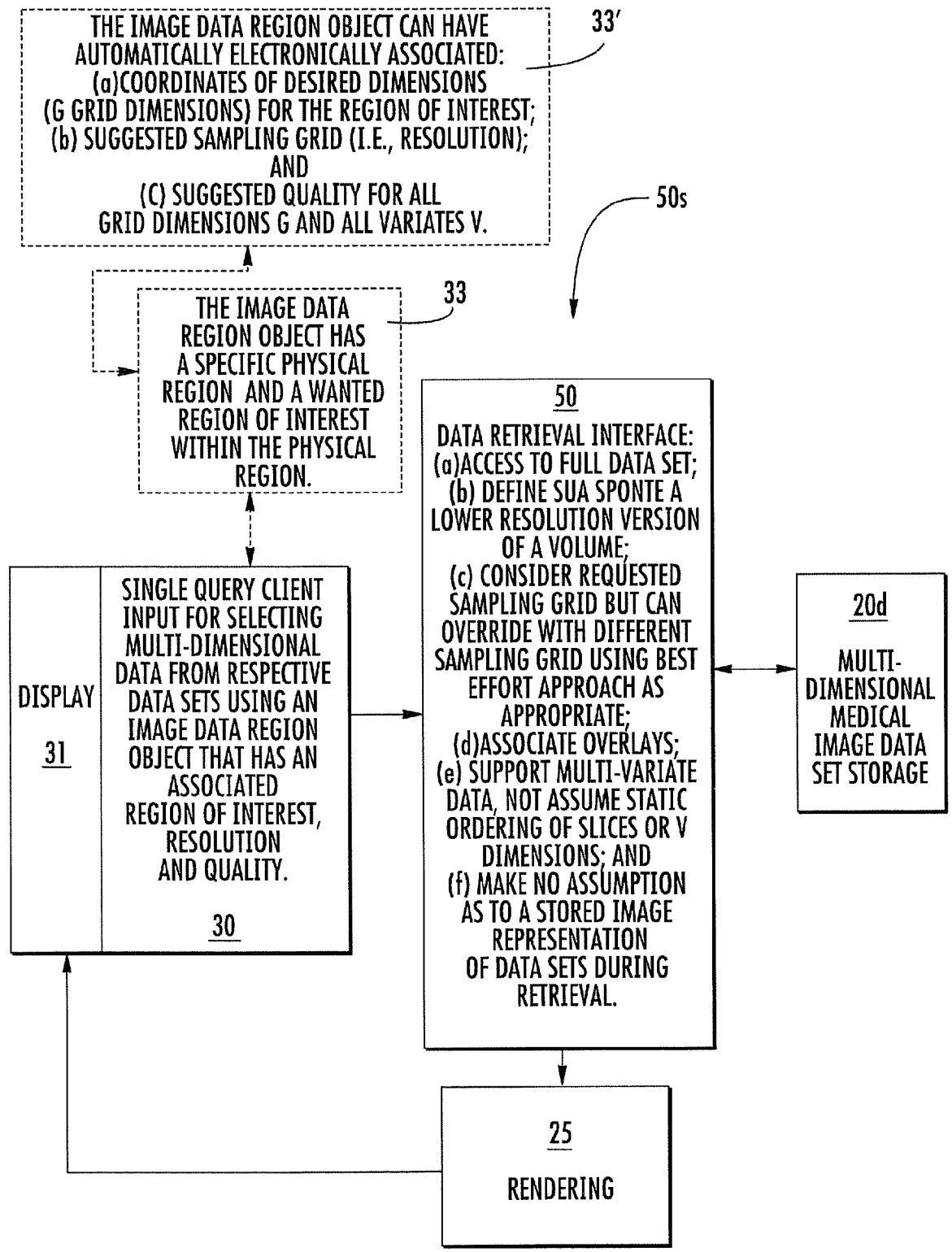
FIG. 7 is a block diagram of a medical visualization system according to embodiments of the present invention.

FIG. 7 illustrates another example of a data retrieval system 50s. As shown, a client 30 can be configured to employ a single query client input for selecting multi-dimensional data from respective data sets using an Image data region object that has an associated region of interest, resolution and quality. The Image data region object 33 can have a specific physical region and a wanted region of interest within the physical region. The Image data region object may optionally have automatically electronically associated parameters of one or more of: (a) coordinates of desired dimensions (G grid dimensions) for the region of interest; (b) suggested sampling grid (i.e., resolution); and (c) suggested quality for all grid dimensions G and all variates V.

The data retrieval interface 50 may be configured to: (a) access to full data set; (b) define sua sponte a lower resolution version of a volume than that requested by a client; (c) consider requested sampling grid but can override with different sampling grid using best effort approach as appropriate; (d) associate overlays; (e) support multi-variate data, not assume static ordering of slices or V dimensions; and (f) make no assumption as to a stored image representation of data sets during retrieval of data from the multi-dimensional medial image data set.

In some embodiments, the instant invention can be used to retrieve data of unlimited dimensions and can employ an inexact response to queries to reduce meta data. The data retrieval can be carried out independent of the data representation. The overlay handling can be outside the traditional 2D slice model.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). In some embodiments, some program code may execute on local computers and some program code may execute on one or more local and/or remote server. The communication can be done in real time or near real time or off-line using a volume data set provided from the imaging modality.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 8:
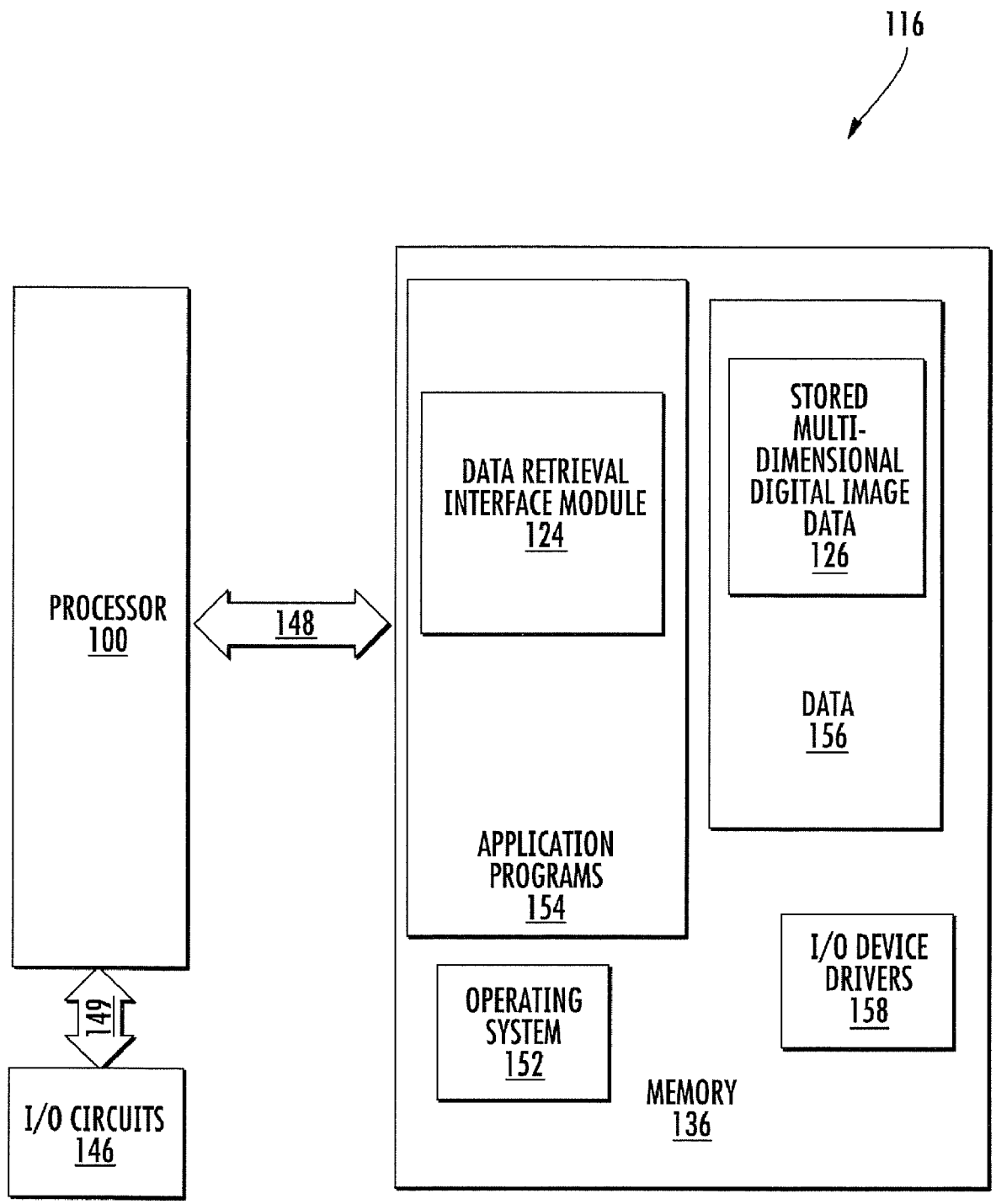
FIG. 8 is a block diagram of a data processing system according to embodiments of the present invention.

As illustrated in FIG. 8, embodiments of the invention may be configured as a data processing system 116, which can be used to carry out or direct operations of the rendering, and can include a processor circuit 100, a memory 136 and input/output circuits 146. The data processing system may be incorporated in, for example, one or more of a personal computer, workstation 116, server, router or the like. The system 116 can reside on one machine or between a plurality of machines. The processor 100 communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 100 can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: ROM, PROM, EPROM, EEPROM, flash memory, SRAM, DRAM and magnetic disk. In some embodiments of the present invention, the memory 136 may be a content addressable memory (CAM).

As further illustrated in FIG. 8, the memory (and/or storage media) 136 may include several categories of software and data used in the data processing system: an operating system 152; application programs 154; input/output device drivers 158; and data 156. As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

The data 156 may include (archived or stored) digital image data sets 126 that provides stacks of image data correlated to respective patients. As further illustrated in FIG. 8, according to some embodiments of the present invention application programs 154 include one or more of: 124. The application programs may also include a DVR Module (not shown) and the data interface module can be decoupled or isolated from the DVR module. The application program 124 may be located in a local server (or processor) and/or database or a remote server (or processor) and/or database, or combinations of local and remote databases and/or servers.

While the present invention is illustrated with reference to the application programs 154, 124 in FIG. 8, as will be appreciated by those of skill in the art, other configurations fall within the scope of the present invention. For example, rather than being application programs 154 these circuits and modules may also be incorporated into the operating system 152 or other such logical division of the data processing system. Furthermore, while the application program 124 is illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 8 but may be provided by other arrangements and/or divisions of functions between data processing systems. For example, although FIG. 8 is illustrated as having various circuits and modules, one or more of these circuits or modules may be combined or separated without departing from the scope of the present invention.

The present invention is explained in greater detail in the following non-limiting Example.

EXAMPLE

Figure 9:
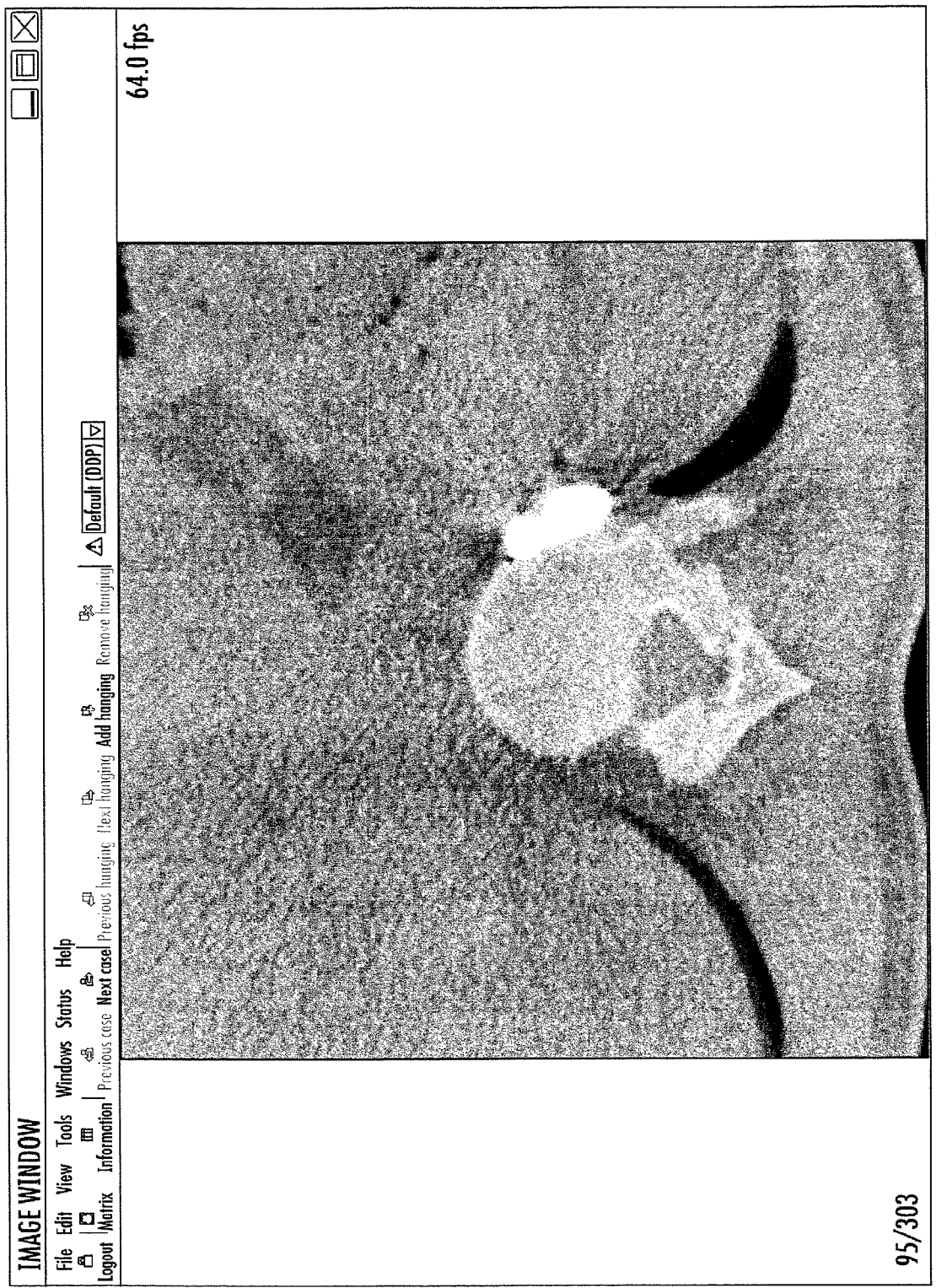
FIG. 9 is a screen shot of a cine-loop image obtained using embodiments of the present invention.

FIG. 9 illustrates a screen capture of a cine-loop image display obtained using a data retrieval interface as described herein. The start-up times are minimal and do not depend on the size of the data set. That is, in the past, looking at the first image of a 1000 slice stack could take 10 times longer than looking at the first image of a 100 slice stack, due the overhead of slice meta data. Start-up time for 3D visualization for large stacks was long, since the full data was sent to the client, even though it then had to be downsampled to fit the graphics card. So, this will be apparent to users as slow start-up times. Although speed is difficult to illustrate in still shots, FIG. 9 is shown for discussion purposes to discuss the speed advantage provided by embodiments of the invention in PACS. As is known to those of skill in the art, a "cine loop" feature refers to looping the slices of a stack. High start-up time means that the frames/second (fps) of the cine-loop will be much slower the first round. With the new data retrieval interface, the systems can operate with a high fps directly. The screen shot shows a first round fps of 64.0.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A data retrieval system for retrieving data from a multi-dimensional medical data set, comprising:
    a client configured to electronically request image data of a patient;
    a server in communication with a plurality of electronically stored multidimensional patient medical image data sets; and
    an electronic data retrieval interface in communication with the client and the server, the data retrieval interface configured to retrieve image data from the multidimensional patient medical data sets, the respective data sets having a number of grid points in G dimensions, and a number of values V for each grid point, wherein some of the data sets have different G dimensions and V values than others,
    wherein the data retrieval interface is configured to employ a Physical region object that defines a multi-dimensional region extent associated with a client request for data on a region of interest to retrieve relevant image data from a respective patient data set, and wherein some of the data sets have grid points in G dimensions such that $G \leq 4$ and at least some have multivariate values for each grid point such that $1 < V \leq 6$ while others have a single value for a respective grid point such that $V=1$.

2. A system according to claim 1, and wherein the data retrieval interface is configured to evaluate a variate number V for a respective patient multi-dimensional data set on-the-fly and does not assume a static ordering of slices or a static number for V.

3. A system according to claim 1, wherein some of the patient data sets have a first static volume with $G=3$ and $V=1$, other patient data sets have a time-dependent volume with $G=4$, and $V=1$, and others have a volume describing flow with $G=3$ and $V=3$, with velocity having a three-dimensional vector.

4. A system according to claim 1, wherein some of the patient data sets comprise MRI image data and some of the patient data sets comprise CT image data.

5. A system according to claim 1, wherein the client is configured to electronically generate an Image data region object to request image data that is transmitted to the data retrieval interface to generate the Physical region object, wherein the Image data region object comprises a desired resolution, quality and coordinates for a multi-dimensional region of interest.

6. A system according to claim 1, wherein the data interface is configured to support queries from clients that include coordinates for a multi-dimensional region of interest, a proposed sampling grid and/or resolution in all G grid dimensions, and a proposed quality for all grid dimensions G and all variates V.

7. A system according to claim 6, wherein the client proposed sampling grid and/or resolution in all G grid dimensions is electronically automatically determined based on a size of a viewport on a display.

8. A system according to claim 5, wherein the client is configured to access desired image data using a single call.

9. A system according to claim 5, wherein the Image data region object electronically: (a) defines coordinates of a 4D region of interest; and (b) automatically defines a suggested sampling grid for all four dimensions of the 4D region of interest.

10. A system according to claim 6, wherein data retrieval interface is configured to electronically alter the sampling grid used to retrieve image data from a full volume patient image data set of the multidimensional imaging data in order to enhance retrieval performance, and wherein the selected image data is transmitted to the client along with the actual sampling grid used to retrieve the image data.

11. A system according to claim 1, wherein the data retrieval interface is configured to electronically automatically associate at least one overlay to image data after the image data is retrieved from the patient data set and before the retrieved image data is sent to the client.

12. A system according to claim 1, wherein the data retrieval interface is configured to electronically communicate with a plurality of clients to retrieve patient data from the server and is further configured: (a) alter, on-the-fly, a sampling grid and/or resolution requested by a respective client; (b) support access to data from data sets having an arbitrary number of dimensions G and variates V; (c) sort and/or group multi-variate data over a volume on-the fly; and (d) electronically associate overlay data to insert text and/or graphical objects that can be displayed in rendered images of retrieved data.

13. A system according to claim 1, wherein the data retrieval interface is modular and configured to operate separated from a data representation module that renders an image view from the retrieved data and transmits the image view to a display at a client workstation whereby the system is not bound by a 2D slice format used by imaging modalities.

14. A system according to claim 1, wherein the client is configured to electronically transmit to the data retrieval interface a viewing specification using an Image data object that identifies a region of interest, desired resolution and desired quality, and wherein the data retrieval interface is configured to determine a physical specification based on a Physical region object that defines an extent of a region, and wherein the data retrieval interface employs a Variate sorting rule object, an Overlay object and a Frame of reference object to retrieve and transmit relevant data from the patient data sets to the client based on the Image data object.

15. A system according to claim 1, wherein the grid dimensions and variates are coupled.

16. A system according to claim 1, wherein the grid dimensions and variates are independent.

17. A system according to claim 1, further comprising a rendering module in communication with the client and data retrieval interface, wherein the rendering module is separate from the data retrieval interface.

18. A system according to claim 1, wherein the client and data retrieval interface are configured to employ object-oriented communication protocols to identify and retrieve relevant data to thereby reduce meta data.

19. A signal processor circuit comprising a data retrieval interface module in communication with a client and a server for extracting data from respective patient multidimensional imaging data sets obtained from different imaging modalities, wherein the signal processor circuit is configured to define a Physical region object to retrieve a subset of image data from a respective multi-dimensional patient image data set that is accessible via the server, wherein the signal processor circuit is configured to define an Image data region object that is electronically transmitted to a server in communication with electronically stored multidimensional patient data sets to request image data from a target patient multidimensional imaging data set, wherein the requested image data associated with the Image data region object is then transmitted to the client and used to render a medical image, wherein the data retrieval interface module is configured to electronically determine on-the-fly a sampling grid used to retrieve image data from the multidimensional imaging data, and wherein the data regarding the sampling grid used to retrieve the image data is transmitted to a client along with the retrieved image data, and wherein the data retrieval interface module is configured to access different data sets with some of the data sets have grid points in G dimensions such that $G \leqq 4$ and at least some have multivariate values for each grid point such that $1 < V \leqq 6$ while others have a single value for a respective grid point, $V=1$.

20. A signal processor circuit according to claim 19, wherein the data retrieval module is configured to determine the number V of a patient multi-dimensional data set on-the-fly and does not assume a static ordering of slices or a static number for V.

21. A signal processor circuit according to claim 19, wherein the data retrieval module is configured to operate with different types of data sets where some of the patient data sets have a first static volume with $G=3$ and $V=1$, other patient data sets have a time-dependent volume with $G=4$, and $V=1$, and others have a volume describing flow with $G=3$ and $V=3$, with velocity having a three-dimensional vector.

22. A signal processor circuit according to claim 19, wherein the data retrieval interface module is configured to electronically automatically associate at least one overlay to image data after the image data is retrieved from the patient data set and before the retrieved image data is sent to a client.

23. A signal processor circuit according to claim 19, wherein the data retrieval interface module is configured to electronically communicate with a plurality of clients to retrieve patient data from a server and is further configured to: (a) retrieve data from data sets having any number of dimensions G and variates V; (b) sort and/or group multi-variate data over a common volume on-the fly; and (c) electronically associate overlay data to insert text and/or graphical objects that can be displayed with rendered images of the retrieved patient data.

24. A signal processor circuit according to claim 19, wherein the data retrieval interface is modular and configured to operate separated from a data representation module that renders the image view from the retrieved data circuit is not bound by a 2D slice format used by imaging modalities.

25. A physician workstation with a display comprising an object-oriented data retrieval module configured to: (a) receive a single image data region query from the physician workstation to initiate a data retrieval operation, the single query is configured to employ a Physical region object that defines a multi-dimensional region extent associated with a request for data on a region of interest to retrieve relevant image data from a respective patient data set including defining resolution, quality and multi-dimensional coordinates of an anatomical region of interest of a patient; and (b) electronically retrieve relevant patient image data from a multi-dimensional data set, then transmit the relevant data to the workstation display with data regarding a sampling grid employed to obtain the relevant patient image data, wherein some of the data sets have grid points in G dimensions such that $G \leq 4$ and at least some have multivariate values for each grid point such that $1 < V \leq 6$ while others have a single value for a respective grid point such that $V=1$.

26. A workstation according to claim 25, wherein the data retrieval module is configured to determine a sampling grid used to retrieve image data based on an on-the-fly algorithm corresponding to a type of data set, an end representation view, and a size of a viewport on a display at a workstation.

27. A computer program product for providing physician interactive access to patient medical volume data for retrieving data for rendering diagnostic medical images, the computer program product comprising:
  a computer readable storage medium having computer readable program code embodied in the medium, the computer-readable program code comprising:
  computer readable program code configured to generate a first object associated with a viewing specification of an image data region of interest from at least one client;
  computer readable program code configured to generate a second object associated with an electronic physical specification based on data from the viewing specification;
  computer readable program code configured to retrieve relevant patient image data from a server having digital multi-dimensional patient image data sets using data from at least one of the first and second objects, wherein the computer readable program code configured to retrieve relevant data from a server having digital multi-dimensional patient image data sets is configured to support access to data from data sets having an arbitrary number of dimensions G and variates V using data from at least one of the first and second objects;
  computer readable program code configured to render and display medical images using the retrieved patient image data;
  computer readable program code configured to sort and/or group multi-variate data over a volume on-the fly, wherein the computer readable program that is configured to retrieve relevant data is configured to alter, on-the-fly, a sampling grid and/or resolution requested by a respective client; and
  computer readable program code configured to electronically associate overlay data to insert text and/or graphical objects that can be displayed with rendered images of the retrieved relevant data.

28. A computer program product for providing physician access to patient medical volume data using a networked system that retrieves data from patient image data sets for rendering diagnostic medical images, the computer program product comprising:
  a computer readable storage medium having computer readable program code embodied in the medium, the computer-readable program code executable on one or more processors and comprising:
  computer readable program code configured to allow clients of a networked system to request image data of a region of interest from a respective patient multi-dimensional image data set; and
  computer readable program code configured to define a first object that represents the request for multi-dimensional image data of a respective patient for a region of interest, the first object identifying coordinates of the region of interest, a proposed sampling grid and/or resolution, and a proposed quality for each dimension associated with the requested image data,
  wherein the respective data sets have a number of grid points in G dimensions, and a number of values V for each grid point, wherein some of the data sets have different G dimensions and V values than others, and wherein some of the data sets have grid points in G dimensions such that $G \leq 4$ and at least some have multivariate values for each grid point such that $1 < V \leq 6$ while others have a single value for a respective grid point such that $V=1$.

29. A computer program product for providing access to patient medical data sets using a networked system for retrieving desired patient image data from multi-dimensional patient image data sets for rendering diagnostic medical images, the computer program product comprising:
  a computer readable storage medium having computer readable program code embodied in the medium, the computer-readable program code executable on one or more processors and comprising:
  computer readable program code configured to allow clients of a networked system to request image data of a physical region of interest from a remote server; and
  computer readable program code configured to provide a first object that represents a spatial extent of a physical region of a region of interest identified in a call from a client for the requested image data; and
  computer readable program code configured to provide a second object that represents an overlay that can electronically associate text and/or graphic data with image views of data in the physical region of interest,
  wherein the respective data sets have a number of grid points in G dimensions, and a number of values V for each grid point, wherein some of the data sets have different G dimensions and V values than others, and wherein some of the data sets have grid points in C dimensions such that $G \leq 4$ and at least some have multivariate values for each grid point such that $1 < V \leq 6$ while others have a single value for a respective grid point such that $V=1$.

30. A computer program product according to claim 29, further comprising:
  computer readable program code configured to provide a third object that represents a frame of reference associated with the physical region that is used to extract relevant data from the patient data set; and
  computer readable program code configured to provide a fourth object that represents a variate sorting rule that defines how multivariate data in the patient image data set is to be grouped or sorted.

31. A system according to claim 1, further comprising:
  a rendering module in communication with the client and the data retrieval interface, wherein the rendering module is configured to electronically render patient medical images using the retrieved image data from a respective patient data set; and a workstation having (a) a user input in communication with the client to allow a user to request image data of respective patients using the data retrieval interface and (b) a display in communication with the rendering module, wherein the display displays the rendered respective patient medical images using the retrieved image data.

* * * * *

UNITED STATES PATENT AND TRADEMARK OFFICE
CERTIFICATE OF CORRECTION

PATENT NO. : 7,689,539 B2 Page 1 of 1
APPLICATION NO. : 11/560889
DATED : March 30, 2010
INVENTOR(S) : Sjöblom et al.

It is certified that error appears in the above-identified patent and that said Letters Patent is hereby corrected as shown below:

In the Claims
Column 20, Line 47, Claim 29: Please correct "have grid points in C"
to read --have grid points in G--.

Signed and Sealed this

Twenty-ninth Day of June, 2010

David J. Kappos
*Director of the United States Patent and Trademark Office*